United States Patent [19]

Rosemeier et al.

[11] 4,265,428

[45] May 5, 1981

[54] CONNECTION DEVICE FOR PROVIDING SELECTIVE FLUID COMMUNICATION BETWEEN FIRST AND SECOND CONDUITS

[75] Inventors: Friedrich Rosemeier, Hechingen; Horst Killmaier, Hechingen-Boll, both of Fed. Rep. of Germany

[73] Assignee: Gambro Dialysatoren GmbH & Co. KG, Fed. Rep. of Germany

[21] Appl. No.: 74,323

[22] Filed: Sep. 11, 1979

[30] Foreign Application Priority Data

Sep. 13, 1978 [SE] Sweden ............................ 7809624

[51] Int. Cl.³ ............................................ F16K 31/44
[52] U.S. Cl. .................................. 251/346; 251/342; 251/351; 251/347
[58] Field of Search ............... 251/342, 349, 351, 352, 251/353, 346, 347

[56] References Cited

U.S. PATENT DOCUMENTS

| 2,538,211 | 1/1951 | Prout ............................ 251/351 X |
| 3,685,795 | 8/1972 | Caster .......................... 251/342 |
| 3,707,972 | 1/1973 | Villars et al. ................ 251/342 X |
| 3,971,541 | 7/1976 | Griffin ......................... 251/342 |
| 4,056,116 | 11/1977 | Carter et al. .............. 251/342 X |
| 4,177,949 | 12/1979 | Curtis .......................... 251/351 X |

*Primary Examiner*—William R. Cline
*Attorney, Agent, or Firm*—Lerner, David, Littenberg & Samuel

[57] ABSTRACT

A connection device for connection to first and second fluid conduits for providing selective fluid communication between the two conduits. The connection device comprises a first member having first and second open ends and a fluid passageway therebetween, and a second member having a first open end and a second end with a fluid passage defined therebetween and in which the second end is disposed within the second open end of the first member. The first and second members are movable relative to one another between an open position in which the first fluid passageway in the first member and the second fluid passageway in the second member are in fluid communication with one another, and a closed position. Closure means are provided associated with the second ends of at least one of the first and second members for closing one of the first and second passageways to prevent the fluid communication therethrough between the first ends of the first and second members when the second member is in a closed position. Bias means are provided for biasing the second member towards the closed position when the second member is moved towards the open position.

9 Claims, 3 Drawing Figures

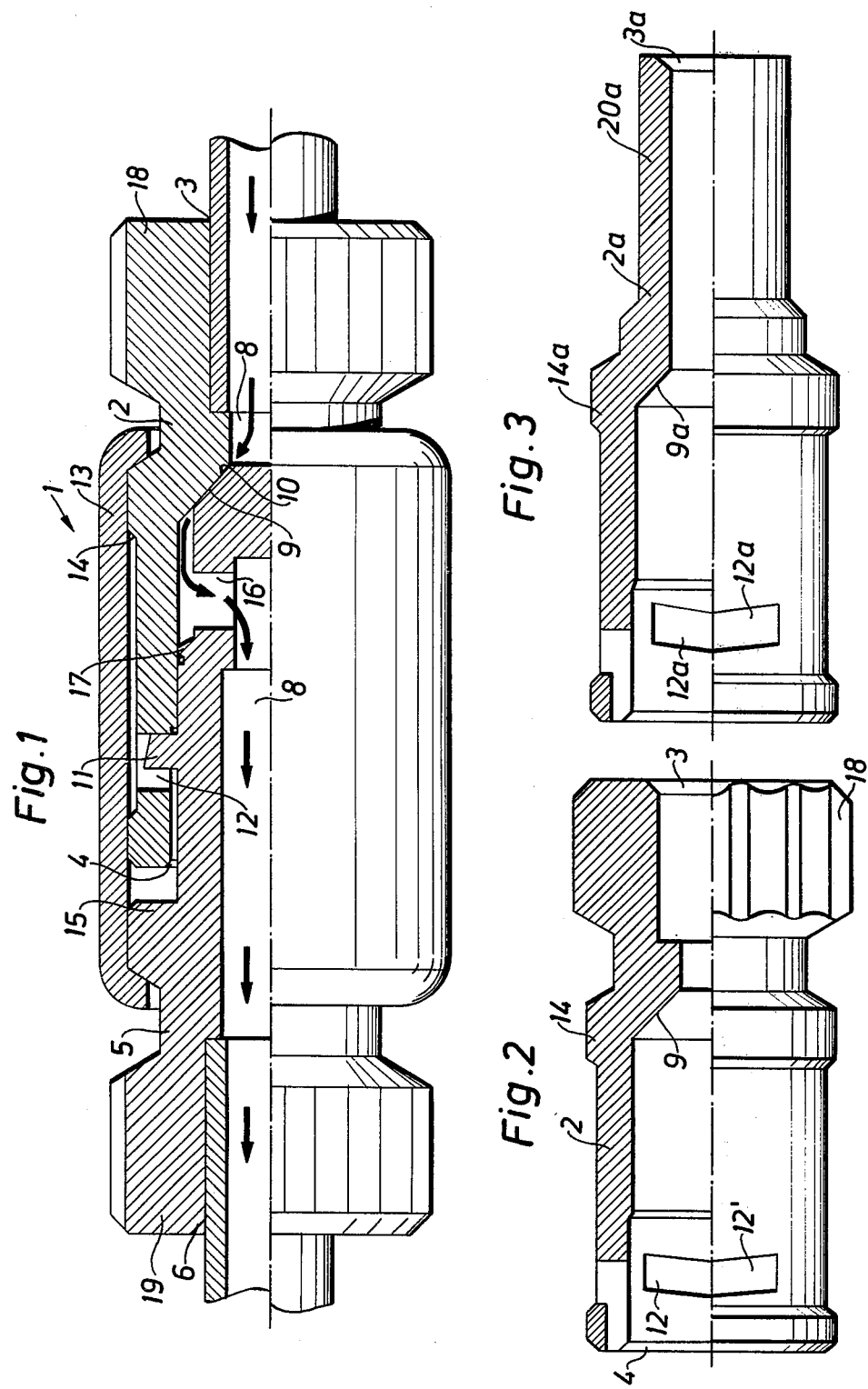

CONNECTION DEVICE FOR PROVIDING SELECTIVE FLUID COMMUNICATION BETWEEN FIRST AND SECOND CONDUITS

BACKGROUND OF THE INVENTION

The present invention relates to connection devices for providing fluid communication between first and second fluid conduits, and more particularly, to a connection device for providing selective fluid communication between such fluid conduits.

Many different types of fluid connection devices for providing fluid communication between respective fluid conduits or containers are well known and have been used for a variety of purposes. For example, coupling devices have been proposed for blood tubes which are each connected to a blood bag for providing fluid communication between the respective blood bags through the intermediary of the respective tubes and connecting devices. Also, it is known that one end of such a connecting or coupling device could be directly coupled to a blood bag without a connecting tube, and the other end of the connecting or coupling device coupled to a second blood bag by the intermediary of a tube so that the bags would be interconnected by the tube and the connecting or coupling device.

With these prior art type devices, the coupling device is generally integrally manufactured and has open ends as well as an intermediate passageway connecting these ends so that when the respective ends of the tubes (or the end of the blood bag or container and a tube) are coupled to the opposing open ends of the coupling device, fluid communication is provided through the passageway of the connecting device. As may be readily appreciated, with such an arrangement the connection between the tubes cannot be broken other than by disconnection of the connecting device, or by compression (if flexible tubes are used) of one or the other of the tubes to stop the flow of fluid. This has often caused problems, particularly when the tubes have been connected to blood bags and blood has flowed therethrough for filling or emptying of the bag. Irrespective of the alternative which is selected for causing fluid communication to stop, be it disconnection and/or compression, unnecessary loss of blood has occurred.

An object of the present invention therefore is to provide a connection device which is particularly useful for connecting of fluid conduits for carrying of blood and the like which not only makes possible fluid connection between the conduits but also is capable of providing rapid discontinuation of the fluid communication while the fluid conduits remain coupled to the connecting device. A further object of the present invention is to provide such a connecting device which also makes possible the discontinuation of fluid communication without the need of compressing or constricting any of the connected conduits.

SUMMARY OF THE INVENTION

In accordance with the present invention there is provided a connection device for connection to first and second fluid conduits for providing selective fluid communication between the two conduits. The connection device comprises a first member having first and second open ends and a fluid passageway therebetween, and a second member having a first open end and a second end with a fluid passage defined therebetween and in which the second end is disposed within the second open end of the first member. The first and second members are movable relative to one another between an open position in which the first fluid passageway in the first member and the second fluid passageway in the second member are in fluid communication with one another, and a closed position. Closure means are provided associated with the second ends of at least one of the first and second members for closing one of the first and second passageways to prevent the fluid communication therethrough between the first ends of the first and second members when the second member is in a closed position. Bias means are provided for biasing the second member towards the closed position when the second member is moved towards the open position.

In this way, the connection device provides for selective fluid communication between the first and second fluid conduits through the connection device. When the second member is in the closed position, the flow of fluid therethrough is stopped whereas when the second member is in the open position, the first and second passageways are in fluid communication with one another to allow the flow of fluid between the two conduits. The bias means serves to hinder movement of the second member towards the open position which is particularly useful with blood lines and the like to only permit the flow of fluid through the connection device under a positive action in moving the second member toward the open position. In the preferred embodiment, the bias means also serves to assist in movement of the second member toward the closed position to prevent fluid flow therethrough. Thus, the second member may be easily moved to the closed flow-preventing position whereas it is more difficult to move the second member toward the flow-permitting or open position.

Also in accordance with the preferred embodiment of the present invention, the biasing force exerted by the bias means increases to a greater extent as the second member is moved toward the flow opening position so that the greatest force exerted by the biasing means exists when the second member is in the full open position. Similarly, the biasing force decreases as the second member is moved toward the closed position.

Further in accordance with the preferred embodiment, the bias means comprises a resilient casing or sleeve member which is engagingly disposed about the first and second members and in firm contact therewith. Because of the resilience of the casing and the firm contact thereof with the first and second members, the casing serves as a spring which hinders or assists respectively movement of the second member toward the open position and toward the closed position.

The first member preferably includes a seating surface intermediate the first and second ends which is adapted to sealingly abut with a corresponding seating surface on the second end of the second member when the second member is in the closed position. Preferably, the sealing surface is annular and conically tapering inwardly and the corresponding seating surface of the second member is also annular and conically tapering toward the second end such that the respective surfaces will abut one another when the second member is located in its furthest inserted position in the first member (i.e., the closed position). When the second member is shifted axially outwardly, a gap is formed between the surfaces which increases as the second member is shifted away from the furthest inserted position in the first member, the second member preferably including a hollow interior which communicates with this gap through a plurality of holes provided in the side walls of the second member adjacent the second end.

Still further in accordance with the preferred embodiment of the present invention, the second member is rotatably disposed within the first member and the axial shifting or movement of the second member is accomplished by such relative rotation. In the preferred embodiment, to accomplish this axial shifting as a result of relative rotation, the second member is provided with suitable guide pins or bosses on its outer circumference which engage in and slide in corresponding grooves or cavities in the first member for guiding movement of the second member to move in a axial direction during relative rotation.

These and further features and characteristics of the present invention will be apparent from the following detailed description in which reference is made to the enclosed drawings which illustrate a preferred embodiment of the present invention.

BRIEF DESCRIPTION OF THE DRAWINGS

FIG. 1 is a side elevational view, partly in section, of the connecting device in accordance with the present invention;

FIG. 2 is a side elevational view, partly in section, of the connecting sleeve or first member of the connecting device shown in FIG. 1; and FIG. 3 is a side elevational view, partly in section, similar to FIG. 2, of an alternative embodiment of the connecting sleeve or first member of the connecting device in accordance with the present invention.

DETAILED DESCRIPTION OF THE PREFERRED EMBODIMENT

Referring now to the drawings wherein like reference characters represent like elements, there is shown in FIGS. 1 and 2 the connecting device in accordance with the preferred embodiment of the present invention. The connecting device is particularly suited for interconnection of blood tubes or other similar types of fluid conduits and medical equipment for extracorporeal treatment of the blood. Accordingly, the present invention will be described with reference to such an application. However, it will be apparent to those skilled in the art that the connection device in accordance with the present invention could also be used in other fields and for other applications where it is desired to provide for selective fluid communication between a pair of conduits adapted to be connected to the opposite ends of the connection device.

As can be seen in FIGS. 1 and 2, the connecting device, generally designated 1, comprises a first member or connecting sleeve 2 having open ends 3 and 4, and a second member or hollow body 5 which is provided with one open end 6 and one closed end 7. The closed end 7 of the hollow body 5 is inserted into the enlarged open end 4 of the connecting sleeve 2 and connected thereto for the formation of a fluid passageway 8 through the connecting device 1 by means of a bayonet catch type lock mechanism.

The hollow body 5 is provided with annular ribs or flanges 17 which are disposed to sealingly abut against the inner wall of the connecting sleeve 2 for sealing the passageway 8 and to prevent possible fluid leakage between the hollow body 5 and the connecting sleeve 2. These ribs or flanges 17 also serve to center, and thus fixedly locate, the hollow body 5 in its axial position within the inner cavity of the connecting sleeve 2.

The hollow body 5 is designed to be axially movable or shiftable relative to the connecting sleeve 2 so that when the hollow body 5 is in its furthermost inserted position, an inwardly conically tapering abutment surface 10 provided at the closed end 7 of the hollow body 5 sealingly abuts with an corresponding annular and conically tapering bottom surface 9 of the connecting sleeve 2 for closing the passageway 8 and preventing the flow of fluid therethrough. The annular abutting sealing surfaces 9, 10 are preferably smooth so that a good seal and abutment is provided when the hollow body 5 is located in its furthest inserted or closed position in the connecting sleeve to completely close off the fluid passageway 8. When the hollow body 5 is shifted axially outward, that is, away from the annular bottom surface 9, a gap is formed between the abutment surfaces 9 and 10, the size of which increases as the hollow body 5 is shifted further away from the closed position in the connecting sleeve 2. This gap defined between the surfaces 9 and 10 forms a communication path between the inner cavities of the connecting sleeve 2 and the hollow body 5 respectively, and moreover, provides means by which the degree of opening of the passageway 8 may be varied to increase and/or decrease the fluid flow through the passageway 8.

Preferably, the hollow body 5 is concentrically and axially shiftable within the connecting sleeve 2 whereby the degree or size of opening of the passageway 8, and thereby the width of the gap between the annular bottom surface 9 and the corresponding abutment surface 10 of the closed end 7 of the hollow body 5, vary uniformly about the closed end 7 of the hollow body 5 during the shifting of the hollow body 5 within the connecting sleeve 2.

In accordance with the preferred embodiment of the present invention, the hollow body 5 is preferably rotatably disposed within the connecting sleeve 2 and means provided so that the axial shifting of the hollow body 5 relative to the connecting sleeve 2 is realized as a result of relative rotation between the hollow body 5 and the connecting sleeve 2, as by a twisting action. In the preferred embodiment, the means for translating the relative twisting motion into relative axial shifting comprises bevelled guide pins or bosses 11 disposed about the outer circumference of the hollow body 5 and which engage in and slide in corresponding guide grooves or cavities 12 in the connecting sleeve 2. As can be appreciated, by varying in a suitable manner the shape of the grooves or cavities 12, such as their degree of inclination or slope, the speed with which the degree of opening of the gap between the abutment surfaces 9 and 10 increases or decreases when the hollow body 5 is twisted within the connecting sleeve 2 can be regulated. The steeper the groove 12 rises, the slower the gap width between the two abutment surfaces 9 and 10 and increases or decreases as the hollow body 5 is twisted. On the other hand, the shallower the groove 12 rises, the faster the gap width increases. Preferably, the connecting sleeve 2 is provided with two such grooves or cavities 12 and the hollow body 5 has two bevelled guide pins 11.

The guide pins 11 conveniently have a bevelled top surface to facilitate the insertion of the hollow body 5 into the connecting sleeve 2, thereby providing for a bayonet type snap catch. Specifically, the guide pin 11 is adapted to be snapped into the groove 12 by compression when the hollow body 5 is inserted into the connecting sleeve 2. This will advantageously assure that the hollow body 5, once inserted into the sleeve 2, is retained within the sleeve 2 without the risk that the two parts 2, 5 will separate from each other. Thus, as is apparent, the pins 11 and cavities 12 serve to unite and mutually retain the hollow body 5 within the connecting sleeve 2 when the two parts are interconnected. For the purposes of symmetry, the grooves 12 and pins 11 are located on mutually opposing sides of the connecting sleeve 2 and hollow body 5 respectively.

In order to further increase the unification and cohesion between the connecting sleeve 2 and the hollow body 5, the connecting sleeve 2 and hollow body 5 are preferably covered by a resilient casing or sleeve member 13 which is shrunk fitted onto these parts 2, 5 or disposed thereon in a suitable manner to cover the two interconnected parts 2, 5. By its resilience, the casing or sleeve 13 acts as a spring which counteracts or assists, respectively, the twisting action between the connecting sleeve 2 and hollow body 5, and thereby the shifting of the hollow body 5 away from or toward, respectively, its innermost position. That is, when the hollow body 5 is twisted outwardly, i.e., such that the degree of opening of the gap between the abutment surfaces 9 and 10 increases, the casing or sleeve 13 will be stretched both axially and circumferentially to a corresponding degree to counteract the twisting. As can be appreciated, the spring action of the casing 13 is greatest when the degree of opening between the abutment surfaces 9 and 10 is greatest. On the other hand, in a corresponding manner, the sleeve 13 will facilitate or assist the inward twisting of the hollow body 5 into the connecting sleeve 2 when the hollow body 5 is twisted in a manner to close the gap between the abutment surfaces 9 and 10. In this regard, as the hollow body 5 is twisted toward the closed position, the spring action of the casing or sleeve 13 decreases to a corresponding degree.

Bosses or flanges 14 and 15 respectively, are arranged about both the hollow body 5 and the connecting sleeve 2 to be overlapped by the ends of the casing or sleeve 13 for secure retention of the sleeve 13 about these parts. Further, it will be appreciated that the casing or sleeve 13 provides the connecting device 1 with an outer surface which is suitably smooth from the viewpoint of hygiene.

As can best be seen in FIG. 1, the hollow body 5 is provided with holes 16 adjacent its closed end 7. These holes 16 are arranged to create fluid communication between the inner cavities of the connecting sleeve 2 between the abutment or sealing surface 9 and the open end 3, and the hollow interior of the hollow body 5 when the hollow body 5 is withdrawn or axially moved away from the abutment surface 9 of the connecting sleeve 2. Thus, the openable and closable passageway 8 through the connecting device 1 according to the present invention is formed in its entirety of the one open end 3 of the connecting sleeve 2, the variable gap between the smooth bottom surface 9 of the connecting sleeve 2 and the corresponding smooth abutment surface 10 of the hollow body 5, the holes 16 and the inner hollow cavity of the hollow body 5 in communication with the open end 6 of the hollow body 5. Thus, when the hollow body 5 is in its open or withdrawn position, fluid may be conducted along this passageway 8 through the connecting device 1. On the other hand, when the hollow body 5 is in its fully inserted or closed position, fluid communication is prevented as a result of the abutment of the smooth surfaces 9 and 10.

Both the connecting sleeve 2 and the hollow body 5 are provided preferably at their respective open ends 3, 6, i.e., the opposing ends of the connecting device 1, with gripping portions 18 and 19 in order to facilitate shifting of the hollow body 5 with respect to the connecting sleeve 2. In the preferred embodiment, these gripping portions 18, 19 are provided with ridges or grooves.

The connecting device 1 of the present invention may be used to provide fluid connection or coupling either between two tubes, or between a tube and a blood bag. Specifically, the one open end 3 of the connecting sleeve 2 may be adapted to be fluid coupled either directly to a blood bag or the like, or indirectly thereto through the intermediary of a tube whose one end is connected directly to the open end 3 of the connecting sleeve 2 while the other end is connected to the blood bag. More specifically, in the embodiment shown in FIGS. 1 and 2, the open end 3 of the connecting sleeve 2 is designed to receive one end of a tubular member which in turn communicates with and is connected to, for example, a blood bag or the like. In this regard, the open end 3 of the connecting tube is provided with a recessed bore into which the end of the tube is inserted, as shown in FIG. 1. Similarly, the other open end of the connecting device, i.e., the end 6 of the hollow body 5, is also provided with a recessed bore for receiving an end of the tube or the like in communication with another blood bag so that fluid communication between the two blood bags may be realized by the intermediary of the pair of tubes and connection device 1.

On the other hand, the open end 3 of the connecting sleeve 2 may be coupled directly to a blood bag for providing fluid communication therewith. FIG. 3 illustrates such an alternative embodiment of the connecting sleeve 2. In this figure, the same reference numerals as used in connection with FIGS. 1 and 2 have been used, but with the addition of the letter "a". The only difference in relation to the above described connecting sleeve 2 illustrated in FIGS. 1 and 2 is that the open end 3a of the connecting sleeve 2a is substantially designed as an elongated shaft which is adapted to be disposed to be insertable and fixedly lockable in a corresponding connecting nipple of a blood bag. Alternatively, the tubular shaft of the open end 3a could be fixedly glued or welded into or onto a suitable seat of the blood bag. The other open end of the connection device (not shown in FIG. 3) is arranged to be coupled to a tube or the like in communication with another blood bag so that fluid communication between the two blood bags may be realized through the intermediary of the tube connected to one end of the connection device 1 and the connection device.

This, it is seen that in accordance with the present invention there is provided a connection device for providing selective fluid communication between a pair of fluid conduits. The connection device 1 comprises a first member or connecting sleeve 2 having first and second open ends 3, 4 and a first passageway defined therebetween, and a second member or hollow body 5 also having first and second ends 6, 7 and defining a fluid passageway therebetween. The second end 7 of the second member 5 is disposed within the second open end 4 of the first member 2 and is axially movable between an open position in which the first and second passageways are in fluid communication with one another to provide for fluid communication through the connecting device 1 and a closed position. Closure means 9, 10 associated with the second end of at least one of the first and second members 2, 5 are provided for closing one of the first and second passageways to prevent fluid communication between the first ends 3, 6 of the first and second members 2, 5 when the second member 5 is in the fully closed position. Bias means, preferably in the form of a connecting sleeve or casing 13, are provided for biasing the second member 5 toward the closed position when the second member 5 is moved toward the open position. In this way, movement of the second member or hollow body 5 toward the open position is hindered whereas movement toward the closed position is assisted. As can be appreciated, this feature is most important since the size of the opening for fluid communication varies depending on the relative position of the second member 5 between the fully closed and fully open positions. The bias means 13 thus provide a means which greatly facilitates accurate regulation and control of the size of the opening, and therefore the amount of fluid which may be conducted through the connecting device 1.

While the preferred embodiment of the present invention has been shown and described, it will be understood that such is merely illustrative and that changes may be made without departing from the scope of the invention as claimed. For example, the cylindrical gripping portions 18 and 19, as shown in the drawings, may be constructed so as to have an oval or some other cross-sectional shape which thereby provides a visual means to determine the degree of opening of the passageway between the abutment surfaces 9 and 10. Such an embodiment of the device, connected to a blood bag, is shown in Swedish design application No. 78,2098, filed Sept. 13, 1978, in Sweden.

What is claimed is:

1. A connecting device for providing selective fluid communication between first and second fluid conduits, said connecting device comprising:
   a first member having a first open end for connection to a first fluid conduit, a second open end, and a first fluid passageway defined between said first and second open ends of said first member, said first fluid passageway including a seating surface between said first and second ends and a hollow interior between said second open end and said seating surface;
   a second member having a first open end for connection to a second fluid conduit, and a second end disposed within said hollow interior of said first end and including a substantially closed end surface having a corresponding seating surface for sealingly mating against said seating surface of said first member, said second member being rotatable relative to said first member, and said second member having a bore extending along substantially the length thereof and further including at least one hole in the sidewall thereof disposed adjacent said second end for providing communication between said hollow interior of said first member and said bore in said second member;
   cooperating guide pins and inclined guide grooves on said first and second members, said guide pins extending radially from one of said first and second members toward the other of said first and second members, and said inclined grooves being provided in the wall of the other of said first and second members for receiving said guide pins so that upon relative rotational movement between said first and second members, said inclined grooves positively axially shift said guide pins and said one member to provide relative axial movement between said first and second members between a closed position in which said seating surface and said cooperating seating surface sealingly mate to prevent fluid communication between said first ends of said first and second members and an open position in which fluid communication is provided from said first end of said first member to said first end of said second member through the gap between said seating surface and said corresponding seating surface of said first and second members, said hollow interior of said first member, said at least one hole in said second member and said bore in said second member;
   sealing means interposed in said hollow interior of said first member between the sidewalls of said first and second members for sealingly enclosing said second end of said second member in said hollow interior of said first member; and
   a resilient sleeve engagable with said first and second members adjacent said first ends thereof for sealingly enclosing said second ends of said first and second members while at the same time permitting relative axial and rotational movement between said first and second members.

2. The connecting device of claim 1 wherein enlarged bosses are provided on the exterior surface of said first and second members for engagement by said resilient sleeve.

3. The connecting device of claim 1 wherein said first and second members are each provided with ridged gripping portions for facilitating relative rotational movement between said second member and said first member.

4. The connecting device of claim 1 wherein there are a plurality of holes provided about the circumference of said second member providing fluid communication between the hollow interior of said second member and said hollow interior of said first member.

5. The connecting device of claim 1 wherein said first end of said first member includes means for connecting said first end of said first member to a fluid container, and wherein said first end of said second member includes means for connecting said second member to a tubular member to provide selective fluid communication between said tubular member and said container through said connecting device.

6. The connecting device of claim 5 wherein said first end of said first member comprises a connecting nipple for being sealingly disposed in a seat of the fluid container and wherein said first end of said second member comprises a bore for receiving the end of the tubular member.

7. The connecting device of claim 1 wherein said first end of said first member includes means for connecting said first member to a first tubular member and wherein said first end of said second member includes means for connecting said second member to a second tubular member for providing selective communication between said first and second tubular members through said connecting device.

8. The connecting device of claim 7 wherein said first ends of said first and second members include bores for receiving said tubular members.

9. The connecting device of claim 1 wherein said sealing means comprises an annular rib on the sidewall of said second member for sealingly abutting against the sidewall of said first member within said hollow interior of said first member.

* * * * *